United States Patent [19]

Ligorati et al.

[11] 3,936,507

[45] Feb. 3, 1976

[54] PROCESS FOR THE PRODUCTION OF 2,2-(4,4'-DIHYDROXY-DIPHENYL)PROPANE

[75] Inventors: Ferdinando Ligorati; Vittorio Emanuele Nova; Giancarlo Aglietti, all of Milan, Italy

[73] Assignee: Societá Italiana Resine S.p.A., Milan, Italy

[22] Filed: Dec. 26, 1973

[21] Appl. No.: 428,576

[30] Foreign Application Priority Data

Dec. 22, 1972 Italy.................................. 33446/72

[52] U.S. Cl. ...... 260/619 A; 260/619 R; 260/621 B
[51] Int. Cl.$^2$ C07C 37/00; C07C 37/20; C07C 37/38
[58] Field of Search ......... 260/619 A, 619 R, 621 B

[56] References Cited
UNITED STATES PATENTS

| | | | |
|---|---|---|---|
| 2,623,908 | 12/1952 | Stoesser et al................. | 260/619 A |
| 3,162,690 | 12/1964 | Marx et al. ...................... | 260/619 A |
| 3,169,996 | 2/1965 | Bostian et al................... | 260/619 A |
| 3,326,986 | 6/1967 | Dugan et al. .................... | 260/619 A |
| 3,627,846 | 12/1971 | Meyer.............................. | 260/619 A |

*Primary Examiner*—Norman Morgenstern
*Attorney, Agent, or Firm*—Sughrue, Rothwell, Mion, Zinn & Macpeak

[57] ABSTRACT

A process for the production of 2,2-(4,4'-dihydroxydiphenyl)propane (bisphenol A) of high purity of condensation of phenol with acetone in the presence of strong acids, which comprises
preparing an addition product of bisphenol A and phenol and
separating the constituents of this addition product by fractional condensation of the vapours obtained by treating the addition product at high temperature and at reduced pressure for a short time.

7 Claims, No Drawings

PROCESS FOR THE PRODUCTION OF 2,2-(4,4'-DIHYDROXY-DIPHENYL)PROPANE

BACKGROUND OF THE INVENTION

1. Field of the Invention

The present invention relates to an improved process for the production of 2,2-(4,4' dihydroxydiphenyl)propane, and particularly to a process for the production of 2,2-(4,4'-dihydroxydiphenyl)propane having a high degree of purity.

2. Description of the Prior Art 2,2-(4,4'-Dihydroxydiphenyl)propane, commonly known as "bisphenol A," is the condensation product of two molecules of phenol with one molecule of acetone. The condensation is catalyzed by acidic substances. In practice, bisphenol A is prepared by reaction of acetone with excess phenol in the presence of strong acids and optionally in the presence of accelerators. Usually, sulphuric acid and in particular hydrogen chloride are used as strong acids while mercaptans or mercapto acids are used as accelerators. The reaction yields a crude mixture containing various undesirable by-products in addition to bisphenol A, unreacted phenol and acetone, the acidic catalyst, any activator, and the reaction water. These undesirable by-products include, for example, isomers of bisphenol A having different properties, particularly 2,2-(2,4'-dihydroxydiphenyl)propane and 2,2-(2,2'-dihydroxydiphenyl)propane, complex products such as the so-called "co-dimer" (2,2,4-trimethyl-4-p-hydroxyphenylchroman), condensation products such as trisphenol, even higher condensation products in the form of tarry and high-boiling substances, and decomposition products.

The presence of these by-products involves considerable disadvantages both because of their tendency to remain in the final product and to cause undesirable discolouring of the final product. These tendencies are often pronounced to an extent that the use of the final product is prejudiced, and not only in cases where high purity is required. Moreover, the presence of the decomposition products inhibits some reactions in which bisphenol A usually may be used, for example in the preparation of polycarbonates. The importance of obtaining bisphenol A of high purity therefore seems obvious, and numerous methods have been proposed in the art for this purpose.

According to one of these methods (U.S. Pat. No. 2,191,831), the crude reaction mixture is treated so as to separate bisphenol A directly in crystalline form. However, this is a very complicated and expensive method not only for the numerous washes to which the crystalline bisphenol A must be subjected, but also for the rigorous and careful regulation of the conditions necessary for satisfactory crystallization. Moreover, only rather low yields of bisphenol A are attained.

According to another method (French Pat. No. 1,374,477) the crude condensation mixture is subjected to fractional distillation in order to separate at first the unreacted products and then bisphenol A, which is finally purified by extraction or recrystallization. However, this procedure involves considerable losses of bisphenol A. Additionally, in order to obtain bisphenol A having high purity, repeated extraction or recrystallization is necessary. Thus, even if the distillation is carried out under precautionary conditions, this process involves decomposition of the bisphenol A so that new undesired contaminants are formed, particularly products that give unsatisfactory colour characteristics. Furthermore, complete separation by distillation is often rather difficult and unattainable in practice. This is due to the fact that some components, particularly the isomers of bisphenol A have boiling points very close to bisphenol A.

SUMMARY OF THE INVENTION

It is an object of this invention to provide a simple and economical process for the production of bisphenol A of high purity.

It is a further object of this invention to provide a process for the production of bisphenol A that is devoid of the disadvantages described above.

These objects and others that will become apparent from the following description are accomplished in accordance with this invention, generally speaking, by preparing an addition product of bisphenol A and phenol and separating the constituents of this addition product by fractional condensation of the vapours obtained by treating the addition product at high temperatures and at pressures below atmospheric pressure for a short time.

The addition product of bisphenol A and phenol (in the following description referred to as: the adduct) has a molar ratio of bisphenol to phenol of 1:1.

More particularly, according to the process of the present invention an excess of phenol is reacted with acetone in the presence of an acidic agent at a temperature not exceeding 80°C until the acetone has substantially completely reacted. Then, the acidic agent is removed from the reaction mixture and the bisphenol A contained in the reaction mixture is recovered by crystallization of the bisphenol/phenol adduct. The two constituents of the adduct are finally separated by fractional condensation of the vapours obtained on treatment of the adduct at high temperatures and pressures below atmospheric pressure for a short time.

More precisely, according to the process of the present invention phenol is mixed with acetone in a molar ratio of at least about 2:1 but not exceeding about 10:1. The mixture is then brought to a temperature of between about 40° and 80°C, and an acidic agent, preferably hydrogen chloride, is introduced. The pressure may be varied within the range of from about 1 to 20 atmospheres by adjustment of the feed of gaseous hydrogen chloride. The mixture is held under these conditions for a time of from about 1 to 10 hours, in order to provide substantially complete conversion of the acetone.

The reaction may be carried out continuously or batchwise in one or more reactors.

The hydrogen chloride is removed from the reaction product by usual means. For example, an inert gas may be blown in or the product may be fed into a chamber kept at a low pressure.

The phenol/bisphenol adduct is then crystallized from the degassed crude reaction product. For this purpose, the crude product is first dried, for example by azeotropic distillation of the water-phenol mixture. Hereafter, the anhydrous crude product, is cooled to temperatures below 60°C but not below 35°C.

In order to accelerate the crystallization, usual means may be employed, such as introduction of preformed adduct crystals. Improved purity of the final bisphenol A is attained when the adduct obtained is subjected to washing or recrystallization using a solvent chosen from among aromatic, paraffinic, or chlorinated solvents having boiling points not exceeding about 150°C or using phenol directly.

The washing is carried out using solvent-adduct weight ratios of from about 0.1:1 to 1:1 while the ratios in the crystallization are from about 0.5:1 to 2:1. The crystallization of the adduct and its washing with solvents frequently present certain difficulties due to the viscosity of the phenolic mother liquors. These operations can be facilitated if predetermined quantities of the solvent (from about 10 to 50% by weight with respect to the weight of bisphenol present in the crude product) are added to the crude product to be crystallized. The solvent may also conveniently be added directly in bisphenol A synthesis. The presence of the solvent does not affect the characteristics of the bisphenol A obtained and allows the condensation of phenol and acetone to be carried out at temperatures and with ratios of phenol to acetone lower than the ratios normally used. In a preferred embodiment of the invention, phenol of high purity (at least 99.9%) particularly free from carbonyl compounds, is used as the solvent for washing or crystallization. It should, however, be noted that if commercial phenol is used for washing or recrystallization of the adduct, a bisphenol A having undesirable characteristics, particularly an undesired colour, is obtained.

Furthermore, even when phenol is used for washing or recrystallization, a solvent different from phenol may also be added during bisphenol A synthesis.

The adduct is then melted at a temperature of from about 90° to 120°C. Afterwards, it is fed into a chamber at a pressure below atmospheric pressure and at a temperature above about 180°C and kept in this chamber for a time of not more than about 30 minutes but not less than about 0.1 minute.

In practice, the best results are obtained by using the thin-film technique and employing pressures of from about 1 to 20 mmHg and temperatures of from about 180° to 250°C. In this way bishpenol A and phenol are separated as vapours from the last traces of the coloured and tarry components. The vapours liberated are subjected to fractional condensation so as to separate the bisphenol A at temperatures of from about 160 to 170°C and the phenol at about 45°C. In this way, bisphenol A having a Hazen colour not exceeding 20 and a crystallization point equal to or higher than 156.2°C is obtained. Moreover, in cases where the adduct has been subjected to washing with phenol of high purity, bisphenol A having a Hazen colour not exceeding 10 and a crystallization point equal to or higher than 157°C is obtained directly by fractional condensation. The bisphenol A thus obtained may be used directly in reactions where high purity bisphenol A is required, such as in the production of polycarbonates.

In this description and in the following examples the purity of the bisphenol produced is always expressed and defined on the basis of the colour and the crystallization point. The latter is determined in the usual manner by crystallization of the molten bisphenol at 160°C. The colour is determined by the Hazen method (ASTM D 1209), which essentially comprises dissolving bisphenol A in methanol to give a 50% by weight solution and comparing the colour of this solution with that of standard solutions.

In the fractional condensation, phenol of particularly high purity is recovered in addition to bisphenol A of high purity, so that it can be used advantageously for washing of the adduct.

One of the essential aspects of the process of the present invention is the combination of preparing an adduct of bisphenol A and phenol and separating the two constituents of this adduct by fractional condensation of the vapours obtained under the conditions described. It is already known in the art that bisphenol A can be recovered from the crude condensation product of phenol and acetone by precipitation of its adduct with phenol. Bisphenol A and phenol are then separated by distillation of the melted adduct or by steam distillation. However, these known processes are characterized by low yields of the useful products, in addition to the difficulties occurring in practical performance. Moreover, both the phenol and the bisphenol A separated show insufficient purities. In particular, the bisphenol A has undesirable colour characteristics, which render it unsuitable for use in fields where high purity is required, for example in the preparation of polycarbonates. Moreover, the phenol separated is not suited for use in washing or crystallization of the adduct.

Further advantages are achieved in the process of the present invention when the secondary reaction products separated from the phenolic mother liquors resulting from crystallization of the adduct are recycled to the condensation reaction. In this case formation of by-products is decreased and it is possible to use milder reaction conditions.

The invention will now be further illustrated by the following examples, which are not intended to limit it in any way. All percentages are by weight unless otherwise indicated.

EXAMPLE 1

564 g of phenol and 58 g of acetone were introduced into an autoclave at a pressure of 6 kg/cm$^2$ of anhydrous hydrogen chloride. The temperature rose rapidly and was maintained at 64°C for 2 hours. The reacted mixture was then passed into a degassing tower consisting of a pyrex tube 2.5 cm in diameter and 50 cm in height, packed with 5 × 5 mm Raschig rings, maintained at a temperature of 80°C and at a pressure of 1 atm, where the hydrogen chloride dissolved in the mixture was stripped off. The mixture was then dried by distillation of the waterphenol azeotrope at a pressure of about 20 mmHg and at a temperature of 100°C. The resulting mixture was then cooled to 45°C to crystallize the phenol-bisphenol A adduct, which was separated by filtration from the phenolic mother liquors. 294 g of adduct containing 31.6% of phenol and having a Hazen colour of 30 (50% in methanol) were obtained.

The adduct was melted at a temperature of 100°C and transferred to a thin-film evaporator of the Luwa type maintained at a temperature of 200°C and at a pressure of about 1 mmHg. Phenol and bisphenol A were removed at the top in gaseous form, whereas the last traces of coloured and tarry components separated at the bottom. The vapours separated at the top were subjected to fractional condensation to separate bisphenol A at 160°C and phenol at 45°C.

The bisphenol A obtained had the following characteristics:

Hazen colour (50% in methanol): 20
Crystallization point: 156.2°C
Isomers + co-dimer: 0.3%
Trisphenol: 0.05%
Phenol: 0.01%

EXAMPLE 2 (COMPARATIVE EXAMPLE)

The adduct obtained as in Example 1 was separated into phenol and bisphenol A by simple distillation at a pressure of about 10 mmHg and at a temperature of 160°C.

For this purpose, the adduct melted at a temperature of 100°C was fed continuously into a column 50 cm in height and 2.5 cm in diameter packed with 0.4 × 0.4 cm Raschig rings so as to allow a residence time of 5 minutes. The phenol separated at the top and the bisphenol A at the base of the column. The bisphenol A had the following characteristics:

Hazen colour (50% in methanol): 300
Crystallization point: 155.8°C
Isomers + co-dimer: 0.5%
Trisphenol: 0.07%
Phenol: 0.5%

EXAMPLE 3 (COMPARATIVE EXAMPLE)

The adduct obtained as in Example 1 was separated into phenol and bisphenol A by steam distillation carried out at a pressure of about 10 mmHg and a temperature of 160°C.

For this purpose, the adduct melted at a temperature of 100°C was fed into the column of Example 2, where steam was simultaneously blown in at a ratio of 6 parts by weight of steam per 1 part by weight of adduct. The operating conditions were adjusted so as to allow a residence time of 1 minute. The bisphenol A separated at the base of the column had the following characteristics:

Hazen colour (50% in methanol): 100
Crystallization point: 156.0°C
Isomers + co-dimer: 0.4%
Trisphenol: 0.07%
Phenol: 0.01%

EXAMPLE 4

The adduct obtained in accordance with Example 1 was subjected to washing on a filter with the phenol recovered from the thin-film distillation. This was carried out at a temperature of 45°C and with a weight ratio of phenol to adduct equal to 1. The adduct washed in this way was then subjected to the same operations as in Example 1, under identical conditions. The bisphenol A obtained by condensation of the vapours from the Luwa evaporator had the following characteristics:

Hazen colour (50% in methanol): 10
Crystallization point: 157.0°C
Isomers: 0.03%
Co-dimer: 0.01%
Trisphenol: —
Phenol: 0.01%

EXAMPLE 5

Example 4 was repeated, however, commercial phenol having a titer of 99.8% and containing 500 ppm of carbonyl compounds was used instead of the recovered phenol. The bisphenol A thus obtained, though containing the same amount of impurities as the bisphenol A of Example 4, had a pink colour (Hazen colour: 20; out of tone scale) and was not suited for the production of polycarbonates.

EXAMPLE 6

30 g of isomers and co-dimer recovered by distillation of the phenolic mother liquors resulting from crystallization of the adduct in an earlier cycle and 100 g of toluene were added to the charge of phenol and acetone of Example 1. The condensation reaction was carried out at a temperature of 50°C and at a pressure of 10 kg/cm$^2$ of anhydrous hydrogen chloride for 3 hours. After removal of the hydrogen chloride and drying of the degassed product by distillation of the water-toluene azeotrope, crystallization was carried out at 40°C in the presence of the excess toluene that had not separated in the preceding operation. The adduct was washed on a filter with phenol recovered from an earlier distillation in the Luwa evaporator with a phenol/adduct weight ratio of 30:100. The crystallized and washed adduct was then treated as in Example 1. The bisphenol A thus obtained had the following characteristics:

Hazen colour (50% in methanol): 10
Crystallization point: 157.0°C
Isomers: —
Co-dimer: —
Trisphenol: —
Phenol: 0.01%

EXAMPLE 7

The adduct obtained in accordance with Example 6, instead of being washed with phenol, was crystallized from toluene at a temperature of 50°C. The crystallized adduct was then treated as in Example 6. The bisphenol A thus obtained had the following characteristics:

Hazen colour (50% in methanol): 15
Crystallization point: 157.0°C
Isomers: —
Co-dimer: —
Trisphenol: —
Phenol: 0.01%

What we claim is:

1. A process for the production of 2,2-(4,4'-dihydroxydiphenyl)propane, which comprises the steps of:
  a. reacting phenol with acetone in a molar ratio of phenol to acetone of at least 2:1 and not exceeding 10:1 in the presence of an acid catalyst at a temperature not exceeding 80°C;
  b. removing the acid catalyst and water from the resulting reaction mixture;
  c. crystallizing and separating from said reaction mixture formed in (b) an addition product of 2,2-(4,4'-dihydroxydiphenyl)propane and phenol in a molar ratio of 1:1;
  d. washing or recrystallizing the crystallized addition product using a solvent selected from the group consisting of paraffinic, aromatic and chlorinated hydrocarbons having a boiling point lower than about 150°C and employing weight ratios of solvent to addition product of from about 0.1:1 to 1:1 in the washing and from about 0.5:1 to 2:1 in the crystallization;
  e. melting said separated addition product at a temperature between 90° to 120°C and then vaporizing said melted addition product by thin film evaporation at a temperature of from 180° to 250°C and at a pressure of from 1 to 20 mmHg for a time of from 0.1 to 30 minutes to obtain a gaseous mixture containing phenol and 2,2-(4,4'-dihydroxydiphenol)propane; and f. subjecting said gaseous mixture to fractional condensation, thus separating and recovering said 2,2-(4,4'-dihydroxydiphenyl)propane at a temperature of from about 160° to 170°C and said phenol at a temperature of about 45°C.

2. A process according to claim 1, wherein the crystallization of the addition product is carried out by cooling said reaction mixture formed in step (b) to temperatures of from about 35° to 60°C.

3. A process according to claim 1, wherein the reaction of phenol with acetone is carried out at temperatures of from about 40° to 80°C and at pressures of from about 1 to 20 atmospheres for a time in the range of from about 1 to 10 hours.

4. A process according to claim 1, wherein hydrogen chloride is used as the acid catalyst.

5. A process according to claim 1, wherein the reaction of phenol with acetone is carried out in the presence of a solvent selected from at least one member of the group consisting of paraffinic, aromatic, and chlorinated hydrocarbons having a boiling point lower than about 150°C in a quantity of from about 10 to 50% with respect to the 2,2-(4,4'-dihydroxydiphenyl)propane produced.

6. A process according to claim 1, wherein phenol is used as the solvent in step (d).

7. A process according to claim 6, wherein the phenol recovered in the fractional condensation of the vapors is used as the solvent in step (d).

* * * * *